(12) United States Patent
Ushio et al.

(10) Patent No.: US 7,955,607 B2
(45) Date of Patent: Jun. 7, 2011

(54) METHOD OF EVALUATING EVENNESS OF SUPLATAST TOSILATE CRYSTAL, EVEN CRYSTAL, AND PROCESS FOR PRODUCING THE SAME

(75) Inventors: Takanori Ushio, Tokushima (JP); Keiko Nagai, Kodama-gun (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 1136 days.

(21) Appl. No.: 11/632,075

(22) PCT Filed: Jul. 13, 2005

(86) PCT No.: PCT/JP2005/012893
§ 371 (c)(1),
(2), (4) Date: Jan. 10, 2007

(87) PCT Pub. No.: WO2006/006616
PCT Pub. Date: Jan. 19, 2006

(65) Prior Publication Data
US 2008/0070989 A1 Mar. 20, 2008

(30) Foreign Application Priority Data
Jul. 13, 2004 (JP) ................................. 2004-206046

(51) Int. Cl.
*A61K 31/164* (2006.01)
*A61P 37/08* (2006.01)
*C07C 233/00* (2006.01)
*G01N 21/84* (2006.01)

(52) U.S. Cl. ........... 424/401; 514/625; 356/30; 564/192

(58) Field of Classification Search .................. 424/401
See application file for complete search history.

(56) References Cited

U.S. PATENT DOCUMENTS 5,286,858 A * 2/1994 Moriwaki et al. ............. 540/560
6,458,798 B1 * 10/2002 Fujita et al. ................. 514/260.1
2003/0149105 A1 * 8/2003 Ushio et al. ................... 514/553

FOREIGN PATENT DOCUMENTS

| JP | 59-167564 | 9/1984 |
| JP | 07-252213 | 10/1995 |
| WO | 02/083633 | 10/2002 |
| WO | WO02083633 | * 10/2002 |

OTHER PUBLICATIONS

JP-A-1995-252213, Takanori et al., published Mar. 1995. NPL machine translation attached.*
Addadi, et al. "Useful Impurities for Optical Resolutions." J. Am. Chem. Soc. 1981, 103, 1249-1251.*
Takanori Ushio, et al., Polymorphism of an anti-allergic agent suplatast tosilate by Tailor Made Additives, Proceedings of the $122^{nd}$ Annual Meeting of the Pharmaceutical Society of Japan, vol. 3, 26[P] II-193, 26[P] II-194, 26[P] II-195, p. 7 (with English translation), (2002).
Rui Tamura, et al., "Mechanism of Preferential Enrichment, an Unusual Enantiomeric Resolution Phenomenon Caused by Polymorphic Transition during Crystallization of Mixed Crystals Composed of Two Enantiomers", J. Am. Chem. Soc., vol. 124, No. 44, 2002, pp. 13139-13153.
Takanori Ushio, et al., Unusual Enantiomeric Resolution Phenomenon Observed upon Recrystallization of a Racemic Compound, Angew. Chem. Int. Ed. Engl., vol. 35, No. 20, 1996, pp. 2372-2375.

* cited by examiner

*Primary Examiner* — Richard Schnizer
*Assistant Examiner* — Audrea J Buckley
(74) *Attorney, Agent, or Firm* — Oblon, Spivak, McClelland, Maier & Neustadt, L.L.P.

(57) ABSTRACT

Provided are a method for evaluating evenness of suplatast tosilate crystals; stable suplatast tosilate crystals exhibiting evenness in optical purity; and a method for producing the suplatast tosilate crystals.

The method for evaluating evenness of suplatast tosilate crystals includes: (a) a step of adding a solvent to suplatast tosilate crystals to thereby dissolve 3% or less of the crystals in the solvent, and subjecting a portion of the supernatant of the resultant suspension to optical purity measurement, and (b) a step of adding a solvent to the remaining suspension to thereby dissolve the entirety of the suspension in the solvent, and subjecting a portion of the resultant solution to optical purity measurement, wherein the optical purity as measured in the step (a) is compared with the optical purity as measured in the step (b). The suplatast tosilate crystals exhibits excellent evenness and thermal stability. The method for producing the suplatast tosilate crystals is also provided.

10 Claims, 8 Drawing Sheets

METHOD OF EVALUATING EVENNESS OF SUPLATAST TOSILATE CRYSTAL, EVEN CRYSTAL, AND PROCESS FOR PRODUCING THE SAME

TECHNICAL FIELD

The present invention relates to a method for evaluating evenness (as used herein, the term "even(ness)" refers to "RS even(ness)") of suplatast tosilate crystals, which are useful as an antiallergic agent; to even suplatast tosilate crystals; and to a method for producing the suplatast tosilate crystals.

BACKGROUND ART

Suplatast tosilate [(±)-[2-[4-(3-ethoxy-2-hydroxypropoxy)phenylcarbamoyl]ethyl]dimethylsulfonium p-toluenesulfonate] exhibits excellent IgE antibody production suppressing effect, and is a useful therapeutic agent for various allergic diseases (Patent Document 1). As has been known, crystal forms of suplatast tosilate include a crystal form obtained through the method described in Patent Document 1 (hereinafter the crystal form may be referred to as the "first crystal form"); a crystal form described in Patent Document 2 (hereinafter the crystal form may be referred to as the "second crystal form"); a crystal form described in Patent Document 3 (hereinafter the crystal form may be referred to as the "third crystal form"); four crystalline polymorphs; and two solvates (Non-Patent Document 1).

As has been known, anhydrate crystals and hydrate crystals of the same compound exhibits different stabilities, although they have the same crystal form. In evaluation of evenness and stability of such crystals, the ratio between these two types of crystals can be estimated through differential scanning calorimetry or powder X-ray diffractometry, or the degree of stability of these crystals can be determined through measurement of water content. In the case of crystals of poor evenness (e.g., crystals containing amorphous substances), stability of the crystals, which is known to vary with the amount of such amorphous substances contained therein, can be determined through measurement of crystallinity of the crystals. However, with the exception of suplatast tosilate crystals of the first crystal form, there have not yet been reported crystals which are suggested, through measurement data, not to contain, for example, amorphous or other crystalline substances and water, which exhibit the same powder X-ray diffraction pattern, but which exhibit different stabilities. Therefore, needless to say, a method for determining such crystals has not yet been known.

Patent Document 1: Japanese Patent Publication (kokoku) No. 1991-70698
Patent Document 2: JP-A-1995-252213
Patent Document 3: WO 02/083633 pamphlet
Non-Patent Document 1: Proceedings of the 122nd Annual Meeting of The Pharmaceutical Society of Japan, 3, p 7, 26 [P] II-193, 194, 195
Non-Patent Document 2: J. Am. Chem. Soc., 124, 13139-13153 (2002)
Non-Patent Document 3: Angew. Chem. Int. Ed. Engl., 35, 2372-2374 (1996)

DISCLOSURE OF THE INVENTION

The present inventors previously conducted studies on crystalline polymorphs of suplatast tosilate, and considered that suplatast tosilate crystals of the first crystal form (hereinafter may be referred to as "first-form suplatast tosilate crystals") are stable crystals, since all the suplatast tosilate crystals other than first-form suplatast tosilate crystals were transformed into first-form suplatast tosilate crystals. However, despite the inventor's notion that first-form suplatast tosilate crystals is a metastable crystal, it exhibits poor stability at 60° C. compared with suplatast tosilate crystals of the second crystal form (hereinafter may be referred to as "second-form suplatast tosilate crystals") or suplatast tosilate crystals of the third crystal form (hereinafter may be referred to as "third-form suplatast tosilate crystals"), which raised a question among the inventors. In extension research, the present inventors then focused on the reason that explains the poor stability (see Table 1). Because first-form suplatast tosilate crystals are formed on the basis of a specific optical resolution phenomenon (preferential enrichment), and thus the crystals theoretically exhibit an enantiomeric ratio shifted from 1 (Non-Patent Document 2 or 3). However, experiments revealed that the enantiomeric ratio of the thus-formed crystals falls within a range of 0.98 to 1.02; i.e., a shift in enantiomeric ratio from 1 (hereinafter may be referred to as an "enantiomeric ratio shift") was so small that it could be considered to fall within a measurement error. Therefore, it was considered that first-form suplatast tosilate crystals contain crystals of two forms (i.e., the first crystal form and an additional crystal form), and a small amount of the additional-form crystals exhibit poor thermal stability.

TABLE 1

Amount (%) of suplatast tosilate decomposition products produced at 60° C.

| Sample | Lot | Time (month) | Decomposition product 1 | Decomposition product 2 | Decomposition product 3 | Total amount of decomposition products |
|---|---|---|---|---|---|---|
| Invention crystals (Ex. 3) | A | 1 | 0.0 | 0.0 | 0.0 | 0.0 |
|  |  | 2 | 0.0 | 0.0 | 0.0 | 0.0 |
|  |  | 3 | 0.0 | 0.0 | 0.0 | 0.0 |
| Invention crystals (Ex. 4) | B | 1 | 0.0 | 0.0 | 0.0 | 0.0 |
|  |  | 2 | 0.0 | 0.0 | 0.0 | 0.0 |
|  |  | 3 | 0.0 | 0.0 | 0.0 | 0.0 |
| First-form crystals | C | 1 | 0.1 | 0.0 | 0.0 | 0.1 |
|  |  | 2 | 0.6 | 0.3 | 0.2 | 1.1 |
|  |  | 3 | 1.3 | 0.4 | 0.4 | 2.1 |
|  | D | 1 | 0.0 | 0.0 | 0.0 | 0.0 |
|  |  | 2 | 0.4 | 0.2 | 0.1 | 0.7 |
|  |  | 3 | 0.9 | 0.3 | 0.3 | 1.5 |
|  | E | 1 | 0.0 | 0.0 | 0.0 | 0.0 |
|  |  | 2 | 0.3 | 0.1 | 0.1 | 0.5 |
|  |  | 3 | 0.9 | 0.2 | 0.3 | 1.4 |

TABLE 1-continued

Amount (%) of suplatast tosilate decomposition products produced at 60° C.

| Sample | Lot | Time (month) | Decomposition product 1 | Decomposition product 2 | Decomposition product 3 | Total amount of decomposition products |
|---|---|---|---|---|---|---|
| Second-form crystals (ref.) | F | 1 | 0.0 | 0.0 | 0.0 | 0.0 |
| | | 2 | 0.0 | 0.0 | 0.0 | 0.0 |
| | | 3 | 0.1 | 0.1 | 0.0 | 0.2 |
| Third-form crystals (ref.) | G | 1 | 0.0 | 0.0 | 0.0 | 0.0 |
| | | 2 | 0.0 | 0.0 | 0.0 | 0.0 |
| | | 3 | 0.0 | 0.0 | 0.0 | 0.0 |

In view of the aforementioned studies, first-form suplatast tosilate crystals were subjected to powder X-ray diffractometry, differential scanning calorimetry, and infrared absorption spectroscopy, which are generally employed techniques for crystal evaluation. However, any evidence that indicates the co-existence of first-form suplatast tosilate crystals and crystals of additional crystal form could not be obtained. Therefore, a need arose for development of a method for evaluating such additional-form crystals contained in first-form suplatast tosilate crystals. Establishment of such a crystal evaluation method is expected to enable prevention of contamination of first-form suplatast tosilate crystals with a small amount of crystals of additional crystal form, and also is expected to enable development of a method for producing first-form suplatast tosilate crystals of high stability.

Suplatast tosilate is a drug which exhibits a very specific optical resolution phenomenon; i.e., an enantiomeric ratio shift occurs in the mother liquor associated with formation of first-form suplatast tosilate crystals through recrystallization. The present inventors continued studies on the mechanism of this specific optical resolution phenomenon, and almost completely elucidated the optical resolution phenomenon of an ammonium sulfonate compound, which is an analogue of suplatast tosilate. The optical resolution phenomenon of suplatast tosilate has not completely been elucidated, but is considered similar to that of an ammonium sulfonate compound, except for the difference in final crystal form obtained through transition.

Specifically, in the mechanism of production of first-form suplatast tosilate crystals, conceivably, homochiral association between R-enantiomers or between S-enantiomers occurs first in a supersaturated solution to form crystal nuclei, and transition of the crystal nuclei produces heterochiral crystals exhibiting a slight shift in optical purity from 0% ee (hereinafter the crystals may be referred to as "crystals A"); or recombination during formation of crystal nuclei from the homochiral associates produces nuclei of heterochiral crystals A exhibiting a slight shift in optical purity from 0% ee (hereinafter the expression "shift in optical purity from 0% ee" may be referred to as an "optical purity shift"). During production of crystals A, excess homochiral associates are dissociated and redissolved in the solution without being formed into crystals. Thereafter, conceivably, growth of crystals A exhibiting a slight enantiomeric ratio shift gradually increases the optical purity of crystals contained in the mother liquor (Non-Patent Document 2).

The thus-produced crystals A exhibit an optical purity of about 10% ee or less, but exhibit an enantiomeric ratio shift. Therefore, when the optical purity of crystals contained in the supersaturated solution is kept increasing gradually through crystal precipitation, the optical purity will eventually reach such a level that crystals A are no longer produced. Experimental data show that crystals A are difficult to produce when the initial optical purity of crystals contained in the supersaturated solution exceeds 30% ee; virtually no crystals A are produced when the initial optical purity is about 50% ee or more; and no crystals A are produced when the initial optical purity is about 70% ee or more. If the solution is still in a supersaturated state at the time when no crystals A are produced, additional crystals are produced from the associates contained in the solution. Since the solution contains an excessive amount of enantiomers opposite those excessively contained in crystals A, the thus-produced crystals are different from crystals A (hereinafter the different crystals may be referred to as "crystals B"). Properties of crystals B have not yet been elucidated, but are considered to exhibit a large optical purity shift. Therefore, first-form suplatast tosilate crystals of poor stability are considered to contain crystals A and crystals B, and evenness of the suplatast tosilate crystals can be evaluated by determining whether or not crystals B—which come to be mixed in the suplatast tosilate crystals during production thereof—are contained in the suplatast tosilate crystals.

Therefore, firstly, a plurality of lots of first-form suplatast tosilate crystals were compared through infrared absorption spectroscopy, differential scanning calorimetry, and powder X-ray diffractometry, which are generally employed techniques for crystal evaluation. However, no difference was observed between these lots through any of the aforementioned techniques. In addition, conventionally known lots of first-form suplatast tosilate crystals were subjected to optical purity measurement, since first-form suplatast tosilate crystals are known to have a characteristic feature in that the crystals and the mother liquor exhibit an enantiomeric ratio shift during production of the crystals (Non-Patent Document 2 or 3). However, each lot of the crystals exhibited an optical purity of less than 2% ee (i.e., within a range of measurement error), leading to a conclusion that no difference was observed between the lots.

On the basis of these results, the present inventors have conjectured that suplatast tosilate crystals contain a small amount of crystals B of low crystallinity, and thus the amount of crystals B as measured through any of the aforementioned measurement techniques is below the detection limit. Crystals A are known to exhibit an optical purity of about 10% ee or less (Non-Patent Document 2 or 3). Therefore, in the case where suplatast tosilate crystals exhibit an optical purity of 0% ee as a whole, the smaller the amount of crystals B contained in the suplatast tosilate crystals, the higher the optical purity of the crystals B. In such a case, conceivably, the crystals B contain additional crystalline or amorphous substances exhibiting very high optical purity and low crystallinity.

In view of the foregoing, the present inventors have conducted studies on a method for preferentially dissolving crystals exhibiting a large enantiomeric ratio shift, the crystals being contained in suplatast tosilate crystals, and have established a new method for determining mixing of these two types of crystals exhibiting different stabilities. This new method is also a method for evaluating evenness of suplatast tosilate crystals, and as well a method for evaluating crystals exhibiting a large enantiomeric ratio shift, which come to be mixed in third-form suplatast tosilate crystals.

Furthermore, the present inventors have conducted extensive studies on a method for producing suplatast tosilate crystals not containing the aforementioned crystals exhibiting a large enantiomeric ratio shift. In view that mixing of the aforementioned two types of crystals in suplatast tosilate crystals is caused by the mechanism of production of suplatast tosilate crystals, the present inventors have conducted extensive studies for obtaining even crystals of high regularity, and as a result have developed a method for producing suplatast tosilate crystals (hereinafter may be referred to as "suplatast tosilate crystals of the fourth crystal form" or "fourth-form suplatast tosilate crystals") which exhibit a powder X-ray diffraction pattern characteristic of first-form suplatast tosilate crystals, which exhibit high evenness in optical purity (i.e., each of the crystals exhibits an optical purity of about 0% ee), and which exhibit excellent high-temperature stability. The present invention has been accomplished on the basis of these findings.

Accordingly, the present invention provides a method for evaluating evenness of suplatast tosilate crystals, the method comprising: (a) a step of adding a solvent to suplatast tosilate crystals to thereby dissolve 3% or less of the crystals in the solvent, and subjecting a portion of the supernatant of the resultant suspension to optical purity measurement; and (b) a step of adding a solvent to the remaining suspension to thereby dissolve the entirety of the suspension in the solvent, and subjecting a portion of the resultant solution to optical purity measurement, wherein the optical purity as measured in the step (a) is compared with the optical purity as measured in the step (b). The present invention also provides a method for evaluating crystals exhibiting a large enantiomeric ratio shift, which come to be mixed in the third-form suplatast tosilate crystals.

The present invention also provides a method for producing suplatast tosilate crystals exhibiting evenness in optical purity and exhibiting peaks at diffraction angles (2θ±0.1°) in the vicinity of 6.7°, 13.3°, 19.0°, 20.0°, 21.7°, and 22.6° as measured through powder X-ray diffractometry, the method comprising stirring suplatast tosilate crystals in a solvent to thereby induce transition of the crystals, and collecting crystals which, when subjected to optical purity measurement through the aforementioned evaluation method, exhibit an optical purity of less than 2% ee as measured in each of the steps (a) and (b). The production method can efficiently and reliably produce suplatast tosilate crystals exhibiting a powder X-ray diffraction pattern characteristic of first-form suplatast tosilate crystals, and exhibiting high evenness in optical purity (i.e., each of the crystals exhibits an optical purity of about 0% ee). The present invention also provides suplatast tosilate crystals exhibiting evenness in optical purity and high thermal stability, the crystals being produced through the production method. The present invention also provides suplatast tosilate crystals (fourth-form suplatast tosilate crystals) exhibiting evenness in optical purity, exhibiting characteristic peaks at diffraction angles (2θ±0.1°) in the vicinity of 6.7°, 13.3°, 19.0°, 20.0°, 21.7°, and 22.6° as measured through powder X-ray diffractometry, and having a melting point of about 89° C. and a heat of fusion of about 40 KJ/mol as measured through differential scanning calorimetry.

Employment of the evaluation method of the present invention can readily evaluate evenness of suplatast tosilate crystals (i.e., whether or not the suplatast tosilate crystals contain crystals exhibiting a large enantiomeric ratio shift), and can provide a commercial drug containing merely suplatast tosilate crystals of high stability. The production method of the present invention can efficiently and reliably produce suplatast tosilate crystals exhibiting evenness in optical purity and good high-temperature stability.

BEST MODES FOR CARRYING OUT THE INVENTION

Figure 1:
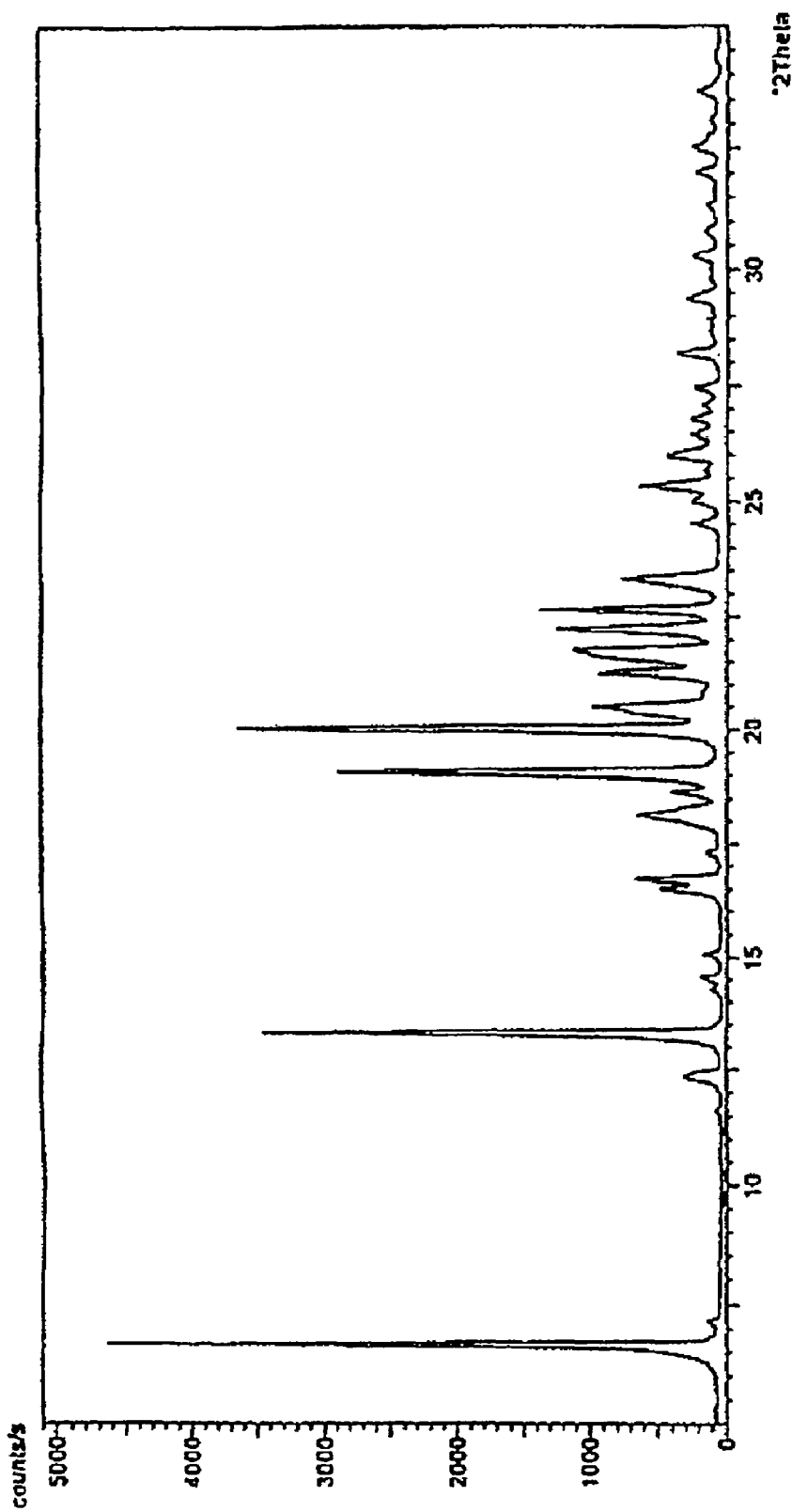
FIG. 1 Powder X-ray diffraction pattern of first-form suplatast tosilate crystals (Example 1). The vertical axis corresponds to X-ray intensity, and the horizontal axis corresponds to diffraction angle (2θ).

In the step (a) of the evaluation method of the present invention, a solvent is added to suplatast tosilate crystals to thereby dissolve 3% (w/v) or less of the crystals in the solvent, and a portion of the supernatant of the resultant suspension is subjected to optical purity measurement. No particular limitation is imposed on the solvent employed in the step (a), so long as it can dissolve suplatast tosilate crystals. If a poor solvent with respect to suplatast tosilate crystals is employed, it may be used in a large amount. Meanwhile, If a solvent having high solubility with respect to suplatast tosilate crystals is employed, it can be used in a small amount, or it may be mixed with a solvent which does not dissolve suplatast tosilate crystals.

Examples of preferred solvents employed in the step (a) include poor solvents with respect to suplatast tosilate crystals, such as 1-propanol, 2-propanol, 2-methylpropanol, 2-butanol, acetone, ethyl acetate, dioxane, diethyl ether, acetonitrile, and tetrahydrofuran. These solvents may be employed singly or in combination. The amount of the solvent employed in the step (a), which varies depending on the type of the solvent, is such an amount that the solvent can dissolve 3% (w/v) or less of suplatast tosilate crystals. From the viewpoint that the amount of the crystals dissolved is controlled to 3% or less, preferably, a poor solvent with respect to the crystals is employed. However, a solvent in which a very small amount of the crystals is dissolved (e.g., hexane or benzene) is not appropriate, since, when the crystals have low optical purity, small peak area is obtained during optical purity measurement by means of, for example, a chiral column, which tends to cause measurement error.

After addition of the solvent, if necessary, the resultant mixture is shaken. When the mixture is shaken, preferably, the resultant suspension is settled until a supernatant is obtained.

Subsequently, the thus-obtained supernatant of the suspension is subjected to optical purity measurement. Optical purity measurement may employ a chiral column; for example, a column filled with cellulose tris(3,5-dimethylphenylcarbamate). The eluent employed may be, for example, a liquid mixture of n-hexane, ethanol, trifluoroacetic acid, and diethylamine. In this liquid mixture, the ethanol content is generally 20 to 25% (w/v), the trifluoroacetic acid content is 0.5% (w/v), and the diethylamine content is 0.1% (w/v). No particular limitation is imposed on the optical purity measuring method, so long as the method enables R and S enantiomers to be separated from each other, and enables an optical purity of 2% ee to be measured.

In the step (b) of the evaluation method of the present invention, a solvent is added to the remaining suspension to thereby dissolve the entirety of the suspension in the solvent, and a portion of the resultant solution is subjected to optical purity measurement. The solvent employed in the step (b) is preferably a solvent having high solubility with respect to suplatast tosilate crystals. Examples of preferred solvents include water, methanol, ethanol, dichloromethane, chloroform, and acetonitrile. These solvents may be employed singly or in combination. No particular limitation is imposed on the amount of a solvent employed, so long as the entirety of the remaining crystals can be dissolved in the solvent. The resultant solution is subjected to optical purity measurement in a manner similar to that described above.

Subsequently, the optical purity obtained through optical purity measurement of the suspension supernatant in the step (a) is compared with the optical purity obtained through optical purity measurement of the solution in the step (b). When no difference in optical purity is observed, the suplatast tosilate crystals tested in the evaluation method are determined even. In contrast, when a difference in optical purity is observed, the suplatast tosilate crystals tested in the evaluation method are determined uneven. More specifically, when the optical purity as measured in each of the steps (a) and (b) is less than 2% ee, the crystals tested are determined even, whereas when the optical purity as measured in at least one of the steps (a) and (b) (particularly in the step (a)) is 2% ee or more, the crystals tested are determined uneven. Such crystals are determined to contain uneven crystalline substances; i.e., the crystals are determined to be crystals containing additional crystalline or amorphous substances of high solubility, having low thermal stability, and exhibiting a large enantiomeric ratio shift (e.g., first-form suplatast tosilate crystals exhibiting a large enantiomeric ratio shift).

As described above, the evaluation method of the present invention evaluates evenness of suplatast tosilate crystals by taking advantage of the difference between the solubility of the crystals in a solvent employed in the step (a) and the solubility of the crystals in a solvent employed in the step (b). Preferably, the solubility of suplatast tosilate crystals in a solvent employed in the step (b) is relatively higher than the solubility of the crystals in a solvent employed in the step (a).

In the case where a solvent appropriately dissolving suplatast tosilate crystals (e.g., 1-propanol, 1-butanol, 2-methylpropanol, or acetonitrile) is employed, a single solvent may be employed for sample preparation in the steps (a) and (b), and the amount of the solvent employed may be regulated in the respective steps (i.e., the amount of the solvent is reduced in the step (a) and increased in the step (b)) for determining evenness of the crystals.

In the evaluation method of the present invention, preferably, the solvent employed in the step (a) is a single member selected from among 1-propanol, 2-propanol, 2-methylpropanol, 2-butanol, acetone, ethyl acetate, dioxane, diethyl ether, acetonitrile, and tetrahydrofuran, or a mixture thereof; and the solvent employed in the step (b) is a single member selected from among water, methanol, ethanol, dichloromethane, chloroform, and acetonitrile, or a mixture thereof. Particularly preferably, the solvent employed in the step (a) is a single member selected from among 2-propanol, acetone, tetrahydrofuran, and ethyl acetate, or a mixture thereof; and the solvent employed in the step (b) is a single member selected from among water, methanol, and ethanol, or a mixture thereof.

The evaluation method of the present invention can readily evaluate evenness of suplatast tosilate crystals, which are widely employed as an antiallergic agent. Through provision of a commercial drug containing merely suplatast tosilate crystals of excellent evenness, the quality of the drug can be secured over a long period of time. The evaluation method provided by the present invention, which evaluates evenness of crystals through optical purity measurement, is based on a new concept, and is widely applicable to evaluation of evenness of racemic crystals (in particular, racemic crystals exhibiting preferential enrichment).

Next will be described the method for producing suplatast tosilate crystals exhibiting evenness in optical purity of the present invention. In the present invention, suplatast tosilate crystals are stirred in a solvent to thereby induce transition of the crystals, to thereby produce suplatast tosilate crystals exhibiting evenness in optical purity. More preferably, suplatast tosilate crystals are stirred in a solvent while the crystals are suspended therein, to thereby induce transition of the crystals. In the production method of the present invention, unlike the case of a recrystallization technique (i.e., crystallization from a highly supersaturated solution), crystals are obtained through transition of suplatast tosilate crystalline polymorphs in a solution of low supersaturation degree. Therefore, the production method can produce stable crystals of high regularity. In addition, the production method, which produces crystals through transition in a solution of low supersaturation degree, can prevent contamination of the crystals with additional crystalline substances.

Examples of the solvent employed for crystal transition include a single solvent selected from among C1-C4 aliphatic alcohols, or a mixture of the solvent and a poor solvent or water; a single solvent selected from among acetonitrile, chloroform, and dichloromethane, or a mixture of the solvent and a poor solvent; a tetrahydrofuran-water solvent mixture; and an acetone-water solvent mixture. Examples of the poor solvent include hexane, cyclohexane, toluene, benzene, diethyl ether, isopropyl ether, methyl acetate, ethyl acetate, methyl ethyl ketone, methyl isobutyl ketone, 2-propanol, 2-butanol, acetone, tetrahydrofuran, and dioxane. From the viewpoints of handling and safety to humans, the solvent which is practically employed for crystal transition is preferably a single solvent such as 1-propanol, 2-propanol, 2-methylpropanol, tetrahydrofuran, acetone, or acetonitrile; a solvent mixture of 2-propanol, 2-butanol, 2-methylpropanol, tetrahydrofuran, or acetone and water, methanol, or ethanol; or a solvent mixture of methanol or ethanol and methyl acetate, ethyl acetate, methyl ethyl ketone, or methyl isobutyl ketone.

In the production method of the present invention, no particular limitation is imposed on the amount of a solvent employed, so long as target crystals can be produced at a predetermined temperature. The solvent is employed in such an amount that suplatast tosilate crystals are dissolved therein in an amount of generally 1 to 30% (w/v), preferably 3 to 20% (w/v), more preferably 3 to 10% (w/v).

The temperature during the course of transition of suplatast tosilate crystals in a solvent, which may be appropriately selected, is generally 0 to 60° C., more preferably 5 to 40° C. During crystal transition at a predetermined temperature, preferably, fourth-form suplatast tosilate crystals are added in an appropriate amount for promoting crystal transition. The amount of fourth-form suplatast tosilate crystals added is generally 10 wt. % or less, preferably 5 wt. % or less. When crystal transition temperature is maintained at a predetermined level, suplatast tosilate crystals may be stirred in a solvent so as to shorten the time required for crystal transition.

"Suplatast tosilate crystals" employed in the production method of the present invention may be any of conventionally known first-form suplatast tosilate crystals (first-form crystals exhibiting unevenness in optical purity; i.e., the optical purity as measured in at least one of the steps (a) and (b) of the aforementioned evaluation method is 2% ee or more), second-form suplatast tosilate crystals, and third-form suplatast tosilate crystals. Alternatively, the suplatast tosilate crystals employed in the production method may be a mixture of these forms of crystals. When solvate crystals are employed, preferably, the solvate crystals are dried before use, since a solvent contained in a large amount in the crystals could cause problems during crystal transition.

First-form suplatast tosilate crystals can be produced through a conventionally known method (e.g., the method described in Japanese Patent Publication (kokoku) No. 1991-70698); second-form suplatast tosilate crystals can be produced through the method described in JP-A-1995-252213; and third-form suplatast tosilate crystals can be produced through the method described in WO 02/083633.

Figure 2:
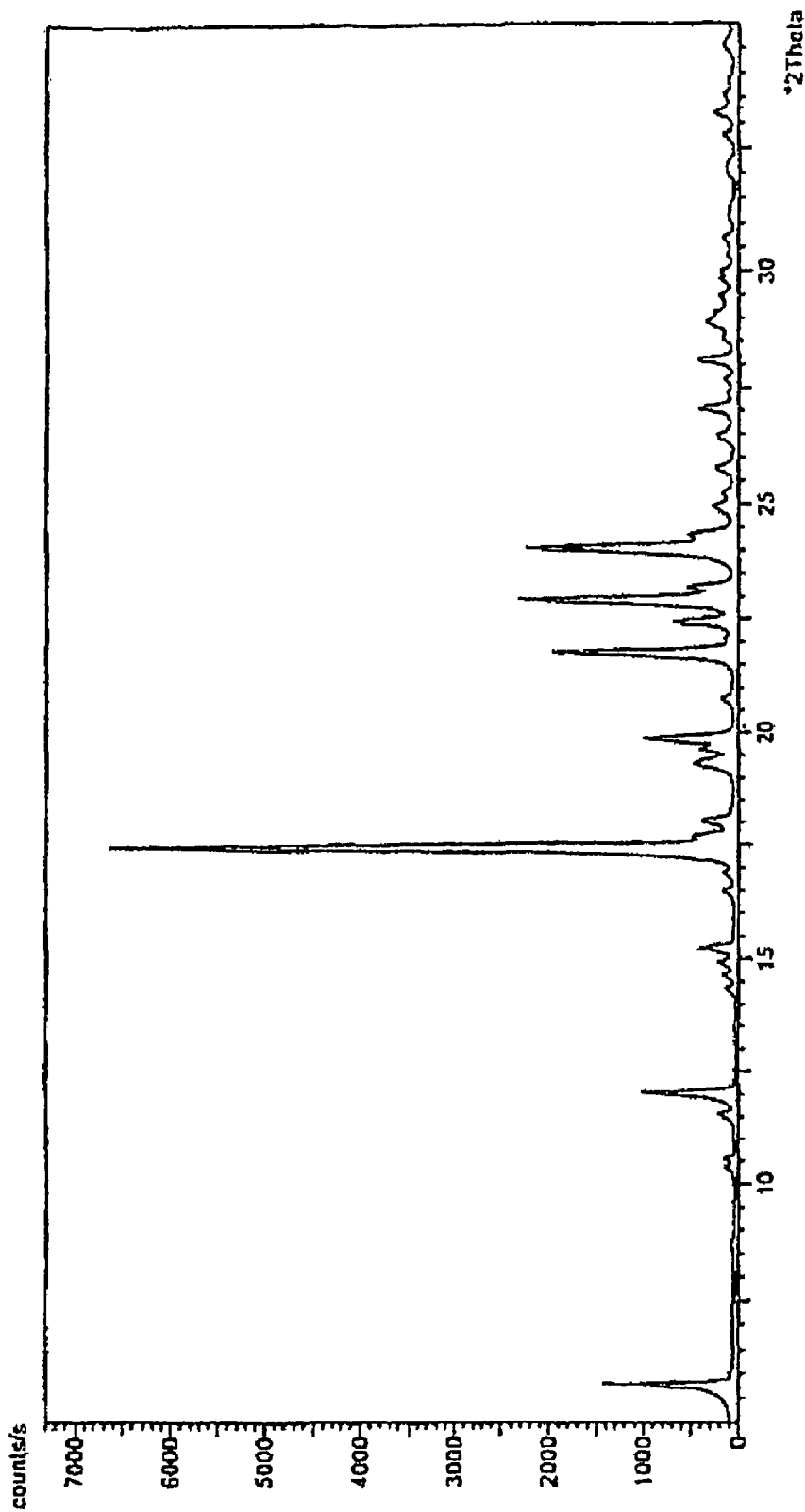
FIG. 2 Powder X-ray diffraction pattern of second-form suplatast tosilate crystals. The vertical axis corresponds to X-ray intensity, and the horizontal axis corresponds to diffraction angle (2θ).
Figure 3:
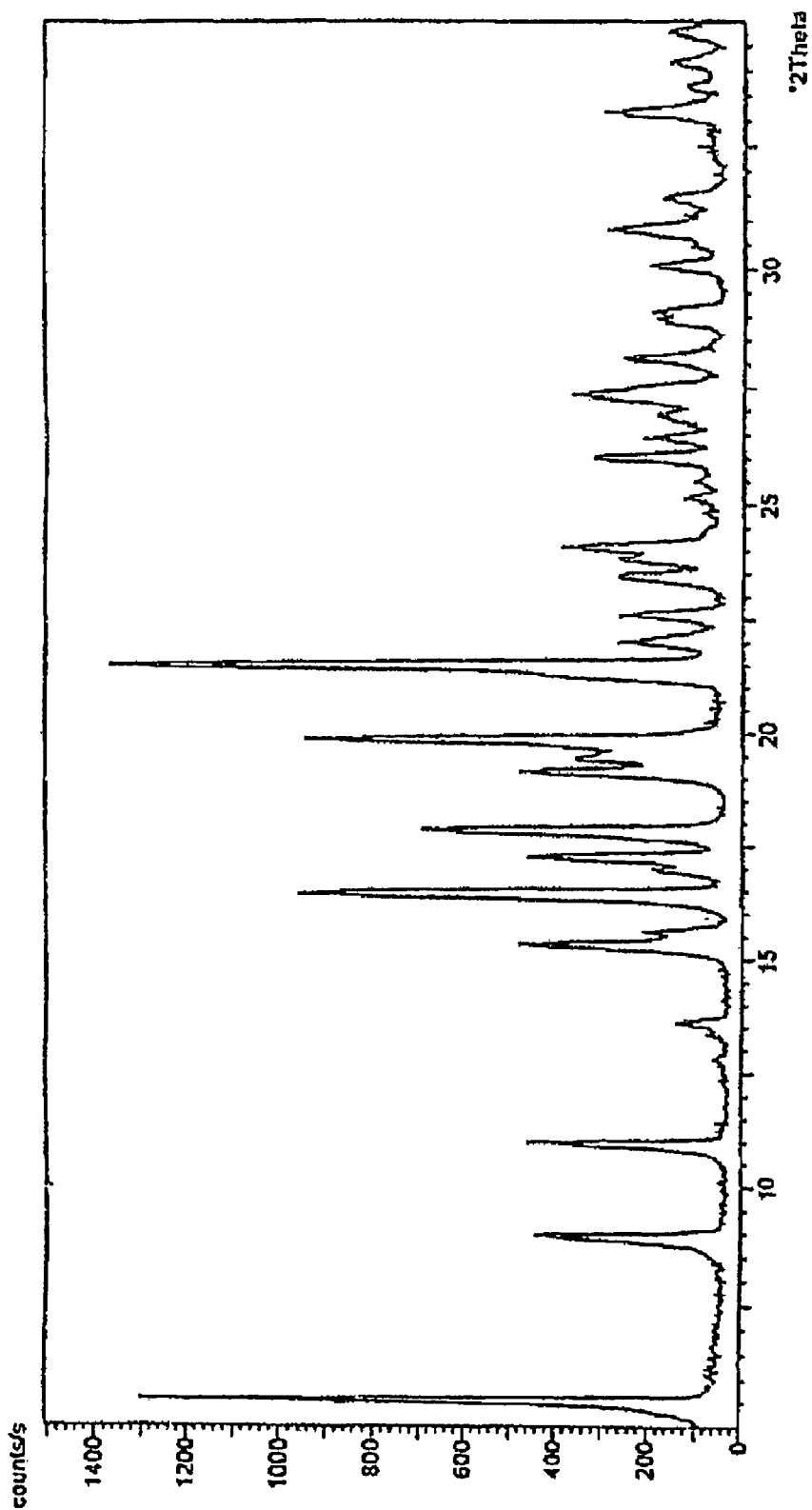
FIG. 3 Powder X-ray diffraction pattern of third-form suplatast tosilate crystals. The vertical axis corresponds to X-ray intensity, and the horizontal axis corresponds to diffraction angle (2θ).

A powder X-ray diffraction pattern of first-form suplatast tosilate crystals produced through the aforementioned known method is as shown in FIG. 1, namely peaks are observed at diffraction angles (2θ±0.1°) of 6.7°, 13.3°, 19.0°, 20.0°, 21.7°, and 22.6°. A powder X-ray diffraction pattern of second-form suplatast tosilate crystals is as shown in FIG. 2, namely peaks are observed at diffraction angles (2θ±0.1°) of 5.7°, 12.0°, 17.4°, 19.8°, 21.7°, 22.9°, and 24.0°. A powder X-ray diffraction pattern of third-form suplatast tosilate crystals is as shown in FIG. 3, namely peaks are observed at diffraction angles (2θ±0.1°) of 5.6°, 9.0°, 11.0°, 15.3°, 16.5°, 17.2°, 17.9°, 19.2°, 19.9°, and 21.5°.

Powder X-ray diffraction data were obtained by means of an X-ray diffractometer (PW3050, product of Philips) employing a vertical goniometer under irradiation with CuKα rays (1.541 Å).

Whether or not crystals produced through the production method of the present invention exhibit evenness in optical purity can be determined on the basis of whether or not the optical purity as measured in each of the steps (a) and (b) of the aforementioned evaluation method is less than 2% ee.

Suplatast tosilate crystals produced through the production method of the present invention exhibit excellent stability and evenness. In the case where suplatast tosilate crystals containing crystals exhibiting low crystallinity and a large enantiomeric ratio shift are dissolved in a small amount of a solvent in the aforementioned step (a), crystals exhibiting low crystallinity and a large enantiomeric ratio shift are preferentially dissolved in the solvent. Therefore, when the solution in which a portion of the crystals is dissolved is subjected to optical purity measurement, the resultant optical purity is shifted from 0% ee. As is clear from measurement data shown in Table 2, conventionally known first-form suplatast tosilate crystals exhibit a large optical purity shift, which is obtained through optical purity measurement of the supernatant of a suspension containing the crystals. In contrast, suplatast tosilate crystals produced through the production method of the present invention exhibit an optical purity of less than 2% ee (i.e., within a range of measurement error).

TABLE 2

Results of optical purity measurement of suplatast tosilate crystals

| Sample | Suspension supernatant | Solution |
| --- | --- | --- |
| Crystals of Example 1 | 0.4% ee (R excess) | 0.1% ee (R excess) |
| Crystals of Example 2 | 1.3% ee (R excess) | 0.0% ee |
| Crystals of Example 3 (Lot A) | 0.0% ee | 0.1% ee (S excess) |
| Crystals of Example 4 (Lot B) | 0.8% ee (R excess) | 0.1% ee (S excess) |
| First-form crystals (Lot C) | 28.4% ee (S excess) | 0.6% ee (R excess) |
| First-form crystals (Lot D) | 42.2% ee (S excess) | 0.6% ee (R excess) |
| First-form crystals (Lot E) | 24.5% ee (S excess) | 0.4% ee (R excess) |

As shown in Table 1, suplatast tosilate crystals produced through the production method of the present invention exhibit high stability at 60° C., as compared with the case of conventionally known first-form suplatast tosilate crystals. In addition, as described below in Table 6, the crystals of the present invention have a melting point of about 89° C. and a heat of fusion of about 40 KJ/mol as measured through differential scanning calorimetry; i.e., the crystals exhibit high thermal stability and evenness in optical purity. Therefore, the crystals of the present invention exhibit very high storage stability as a drug raw material, and are advantageous in terms of quality control.

With or without being crushed, suplatast tosilate crystals produced through the production method of the present invention may be formulated into peroral products (e.g., tablets, capsules, granules, fine granules, and powders), external-use products (e.g., suppositories, inhalants, collunariums, ointments, plasters, and aerosols), and injections. Such a pharmaceutical composition may be produced by use of a pharmaceutically acceptable carrier through a conventional formulation method known to those skilled in the art. A peroral solid product (e.g., tablets, coated tablets, granules, powder, dry syrup, or capsules) can be prepared by adding, to the suplatast tosilate crystals (i.e., active ingredient), an excipient and, if necessary, an additive such as a binder, a disintegrating agent, a lubricant, a coloring agent, a flavoring agent, or a deodorant, followed by customary processing. An injection (a subcutaneous injection, an intramuscular injection, or an intravenous injection) can be prepared by adding, to the active ingredient, a pH-adjusting agent, a buffer, a stabilizer, an isotonizing agent, a local anesthetic agent, or the like, followed by customary processing. A suppository can be prepared by adding, to the active ingredient, an excipient and, if necessary, an additive such as a surfactant, followed by customary processing. An ointment (in the form of, for example, paste, cream, or gel) is formulated by mixing, through a customary technique, the active ingredient with, if necessary, a generally employed additive such as a base, a stabilizer, a humectant, or a preservative. Examples of the base material which may be employed include white petrolatum, paraffin, glycerin, a cellulose derivative, polyethylene glycol, silicone, and bentonite. Examples of the preservative which may be employed include methyl p-hydroxybenzoate, ethyl p-hydroxybenzoate, and propyl p-hydroxybenzoate. A patch can be prepared by applying, to a generally employed support, the aforementioned ointment, cream, gel, or paste, or the like. Examples of appropriate supports include woven fabrics and non-woven fabrics formed of cotton, staple fiber, and chemical fiber; and films and foam sheets formed of soft vinyl chloride, polyethylene, and polyurethane.

Such a pharmaceutical composition is useful, in mammals including human, as a therapeutic drug for allergic diseases (e.g., bronchial asthma, atopic dermatitis, and allergic rhinitis), a therapeutic drug for dysuria, a therapeutic drug for pruritus associated with kidney dialysis, or a therapeutic agent for retroperitoneal fibrosis (Japanese Patent Publication (kokoku) No. 1991-70698, WO 00/27383, JP-A-1999-315019, and JP-A-2005-97220).

The amount of suplatast tosilate crystals incorporated into the aforementioned pharmaceutical composition varies with, for example, the symptom of a patient in need thereof, or the product form of the composition. Preferably, the amount of the crystals per unit dose is about 5 to about 1,000 mg (for a peroral product), about 0.1 to about 500 mg (for an injection), and about 5 to about 1,000 mg (for a suppository or an external-use product). The daily dose of suplatast tosilate crystals contained in the aforementioned pharmaceutical composition, which varies depending on the symptom, etc. of a patient in need thereof, is preferably about 0.1 to about 5,000 mg.

EXAMPLES

The present invention will next be described in more detail by way of Examples, which should not be construed as limiting the invention thereto.

Referential Example 1

First-form suplatast tosilate crystals were produced through the method described in Japanese Patent Publication (kokoku) No. 1991-70698. As shown in FIG. 1, the thus-produced first-form suplatast tosilate crystals exhibited characteristic peaks at diffraction angles (2θ±0.1°) of 6.7°, 13.3°, 19.0°, 20.0°, 21.7°, and 22.6° as measured through powder X-ray diffractometry.

Example 1

Acetone (20 mL) and water (0.05 mL) were added to the first-form suplatast tosilate crystals produced in Referential Example 1 (5.5 g), and the resultant mixture was stirred at 40° C. for 24 hours, followed by further stirring at room temperature for one hour. The thus-produced crystals were collected through filtration. The crystals exhibited a powder X-ray diffraction pattern similar to that of FIG. 1, in which peaks are observed at diffraction angles of 6.7°, 13.3°, 19.0°, 20.0°, 21.7°, and 22.6°. The crystals were subjected to optical purity measurement as described in Example 5. As a result, the optical purity of crystals contained in the supernatant of the suspension was found to be 0.4% ee (R-enantiomer excess), and the optical purity of crystals contained in the solution was found to be 0.1% ee (R-enantiomer excess). Each of the thus-obtained optical purities falls within a range of measurement error, and a large difference is not observed between the optical purities. Thus, even fourth-form suplatast tosilate crystals were produced (Table 2).

Example 2

Acetone (8 mL) and water (0.02 mL) were added to second-form suplatast tosilate crystals (2.0 g) which had been produced through the method described in JP-A-1995-252213, the crystals exhibiting, as shown in FIG. 2, characteristic peaks at diffraction angles (2θ±0.1°) of 5.7°, 12.0°, 17.4°, 19.8°, 21.7°, 22.9°, and 24.0° as measured through powder X-ray diffractometry. In addition, the fourth-form suplatast tosilate crystals produced in Example 1 (0.2 g), serving as seed crystals, were added to the resultant mixture, and the mixture was stirred at 40° C. for 24 hours, followed by further stirring at room temperature for one hour. The thus-produced crystals were collected through filtration. The crystals exhibited a powder X-ray diffraction pattern similar to that of FIG. 1, in which peaks are observed at diffraction angles of 6.7°, 13.3°, 19.0°, 20.0°, 21.7°, and 22.6°. The crystals were subjected to optical purity measurement as described in Example 5. As a result, the optical purity of crystals contained in the supernatant of the suspension was found to be 1.3% ee (R-enantiomer excess), and the optical purity of crystals contained in the solution was found to be 0.0% ee. Each of the thus-obtained optical purities falls within a range of measurement error, and a large difference is not observed between the optical purities. Thus, even fourth-form suplatast tosilate crystals were produced (Table 2).

Example 3

Acetone (40 mL) and water (0.1 mL) were added to third-form suplatast tosilate crystals (10.0 g) which had been produced through the method described in WO 02/083633, the crystals exhibiting, as shown in FIG. 3, characteristic peaks at diffraction angles (2θ±0.1°) of 5.6°, 9.0°, 11.0°, 15.3°, 16.5°, 17.2°, 17.9°, 19.2°, 19.9°, and 21.5° as measured through powder X-ray diffractometry. In addition, the fourth-form suplatast tosilate crystals produced in Example 1 (1.0 g), serving as seed crystals, were added to the resultant mixture, and the mixture was stirred at 40° C. for 24 hours, followed by further stirring at room temperature for about one hour. The thus-produced crystals were collected through filtration. The crystals exhibited a powder X-ray diffraction pattern similar to that of FIG. 1, in which peaks are observed at angles in the vicinity of 6.7°, 13.3°, 19.0°, 20.0°, 21.7°, and 22.6°. The crystals were subjected to optical purity measurement as described in Example 5. As a result, the optical purity of crystals contained in the supernatant of the suspension was found to be 0.0 ee, and the optical purity of crystals contained in the solution was found to be 0.1% ee (S-enantiomer excess). Each of the thus-obtained optical purities falls within a range of measurement error, and a large difference is not observed between the optical purities. Thus, even fourth-form suplatast tosilate crystals were produced (Table 2, Lot A).

Example 4

Acetone (40 mL) and water (0.1 mL) were added to third-form suplatast tosilate crystals (10.0 g) which had been produced through the method described in WO 02/083633, the crystals exhibiting, as shown in FIG. 3, characteristic peaks at diffraction angles (2θ±0.1°) of 5.6°, 9.0°, 11.0°, 15.3°, 16.5°, 17.2°, 17.9°, 19.2°, 19.9°, and 21.5° as measured through powder X-ray diffractometry. In addition, the fourth-form suplatast tosilate crystals produced in Example 1 (1.0 g), serving as seed crystals, were added to the resultant mixture, and the mixture was stirred at 45° C. for five hours, followed by further stirring at room temperature for about one hour. The thus-produced crystals were collected through filtration. The crystals exhibited a powder X-ray diffraction pattern similar to that of FIG. 1, in which peaks are observed at diffraction angles in the vicinity of 6.7°, 13.3°, 19.0°, 20.0°, 21.7°, and 22.6°. The crystals were subjected to optical purity measurement as described in Example 5. As a result, the optical purity of crystals contained in the supernatant of the suspension was found to be 0.8% ee R-enantiomer excess), and the optical purity of crystals contained in a solution was found to be 0.1% ee (S-enantiomer excess). Each of the thus-obtained optical purities falls within a range of measurement error, and a large difference is not observed between the optical purities. Thus, even fourth-form suplatast tosilate crystals were produced (Table 2, Lot B).

Example 5

2-Propanol (0.5 mL) was added to fourth-form suplatast tosilate crystals (0.25 g) produced in each of Examples 1 to 4, and the resultant mixture was shaken and then settled for one hour. Thereafter, a portion (1 μL) of the supernatant of the resultant suspension was applied to a chiral stationary phase column filled with cellulose tris(3,5-dimethylphenylcarbamate) (Chiralcel OD-H, 4.6 mm×25 cm, product of Daicel Chemical Industries, Ltd.) (mobile phase: mixture of n-hexane, ethanol, trifluoroacetic acid, and diethylamine (750:250:5:1)) for optical purity measurement. Subsequently, methanol (2 mL) was added to the remaining suspension to thereby dissolve the crystals therein completely, and the resultant solution was 10-fold diluted. Thereafter, a portion (0.5 μL) of the solution was subjected to optical purity measurement under the same conditions as described above. The results are shown in Table 2.

For reference, first-form suplatast tosilate crystals produced through the method described in Japanese Patent Publication (kokoku) No. 1991-70698 (Lot C, D, or E) were subjected to optical purity measurement in a manner similar to that described above. The results are shown in Table 2.

Thus, the evaluation method of the present invention employing optical purity measurement can readily determine whether or not the thus-produced suplatast tosilate crystals are entirely even.

Example 6

An appropriate amount of each of the solvents described in Table 3 was added to first-form suplatast tosilate crystals produced through the method described in Japanese Patent Publication (kokoku) No. 1991-70698 (Lot C) (0.25 g), and the resultant mixture was shaken and then settled for one hour. Thereafter, a portion (1 μL, or 0.5 μL for the case of addition of 1-propanol) of the supernatant of the resultant suspension was applied to a chiral stationary phase column filled with cellulose tris(3,5-dimethylphenylcarbamate) (Chiralcel OD-H, 4.6 mm×25 cm, product of Daicel Chemical Industries, Ltd.) (mobile phase: mixture of n-hexane, ethanol, trifluoroacetic acid, and diethylamine (750:250:5:1)) for optical purity measurement. Subsequently, an appropriate amount of a solvent corresponding to the above-added solvent was added to the remaining suspension to thereby dissolve the crystals therein completely, and a portion (0.2 μL) of the resultant solution was subjected to optical purity measurement under the same conditions as described above. The results are shown in Table 3.

As is clear from Table 3, first-form suplatast tosilate crystals produced through the conventionally known production method exhibit an optical purity of about 0% ee as a whole, but, when the crystals are dissolved in a small amount in a poor solvent with respect to suplatast tosilate crystals, crystals contained in the supernatant of the resultant suspension exhibit a large optical purity shift. Therefore, the first-form suplatast tosilate crystals exhibit unevenness in optical purity.

TABLE 3

Optical purity (% ee) of first-form suplatast tosilate crystals (Lot C) as measured by use of various solvents

| Suspension supernatant | | | Solution | | |
| --- | --- | --- | --- | --- | --- |
| Solvent | Amount | Optical purity | Solvent | Amount | Optical purity |
| Dioxane | 0.5 mL | 54.7% ee (S excess) | Methanol | 2 mL | 0.4% ee (R excess) |
| Acetone | 0.5 mL | 38.3% ee (S excess) | Methanol | 2 mL | 0.7% ee (R excess) |
| Ethyl acetate | 0.5 mL | 42.5% ee (S excess) | Ethanol | 2 mL | 0.4% ee (R excess) |
| 2-Butanol | 0.5 mL | 47.5% ee (S excess) | Methanol | 2 mL | 0.3% ee (R excess) |
| Diethyl ether | 0.5 mL | 16.2% ee (S excess) | Ethanol | 3 mL | 0.4% ee (R excess) |
| Acetonitrile | 0.5 mL | 20.2% ee (S excess) | Acetonitrile | 4 mL | 0.5% ee (R excess) |
| 1-Propanol | 0.5 mL | 21.7% ee (S excess) | Water | 4 mL | 0.3% ee (R excess) |

Test Example 1

Stability Test

Suplatast tosilate crystals of the present invention produced in Examples 3 and 4 (Lots A and B) and first-form suplatast tosilate crystals produced through the method described in Japanese Patent Publication (kokoku) No. 1991-70698 (Lots C, D, and E) (1.0 g for each Lot) were stored at 60° C. for three months for stability measurement. For reference, second-form suplatast tosilate crystals produced through the method described in JP-A-1995-252213 (Lot F) and third-form suplatast tosilate crystals produced through the method described in WO 02/083633 (Lot G) were subjected to stability measurement in a manner similar to that described above. The results are shown in Table 1.

As is clear from Table 1, all the first-form crystals produced through the conventionally known production method undergo decomposition, but the crystals produced through the production method of the present invention undergo virtually no decomposition and are stable.

Example 7

Figure 4:
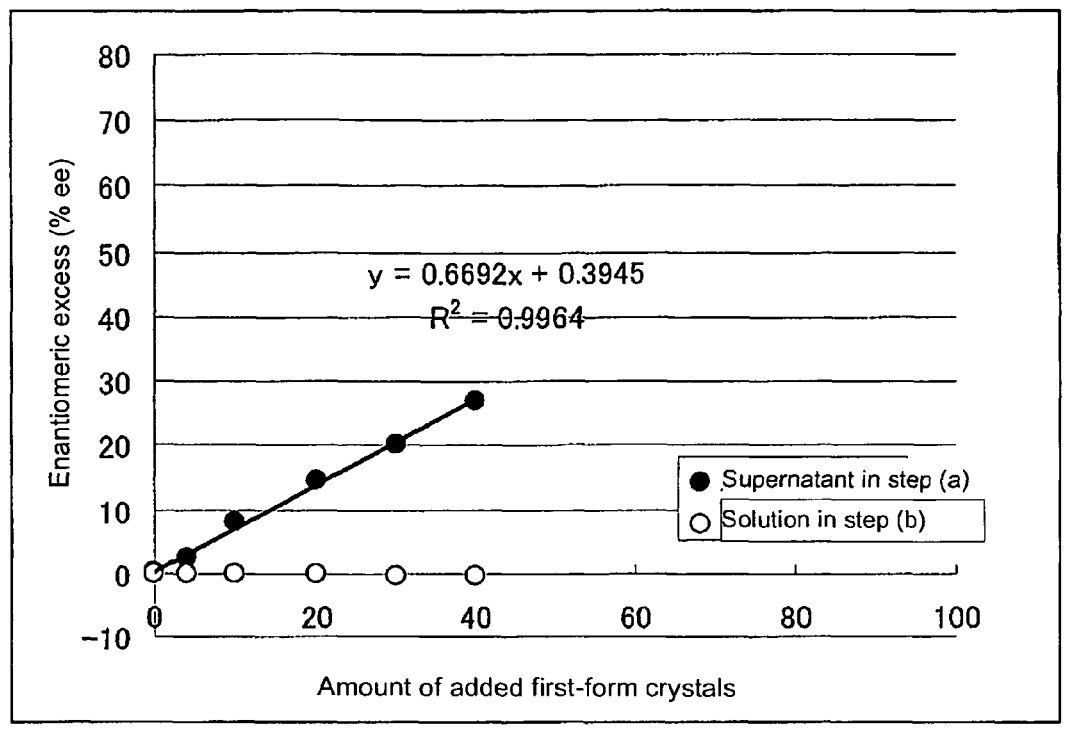
FIG. 4 Graph showing detection of first-form suplatast tosilate crystals present in suplatast tosilate crystals of the present invention.

Suplatast tosilate crystals produced in a manner similar to that described in Example 3 suplatast tosilate crystals produced through the production method of the present invention), which exhibit peaks at diffraction angles in the vicinity of 6.7°, 13.3°, 19.0°, 20.0°, 21.7°, and 22.6°, and first-form suplatast tosilate crystals produced through the method described in Japanese Patent Publication (kokoku) No. 1991-70698 were placed in a sample vial in amounts shown in Table 4, and were mixed together after the vial was capped. 2-Propanol (0.5 mL) was accurately added to the resultant mixture, and the mixture was shaken for 30 seconds and then settled for 30 minutes, followed by centrifugation. A portion (1 μL) of the supernatant of the resultant suspension was applied to a chiral stationary phase column filled with cellulose tris(3,5-dimethylphenylcarbamate) (Chiralcel OD-H, 4.6 mm×25 cm, product of Daicel Chemical Industries, Ltd.) (mobile phase: mixture of n-hexane, ethanol, trifluoroacetic acid, and diethylamine (750:250:5:1)) for optical purity measurement. Subsequently, methanol (2 mL) was added to the remaining suspension to thereby dissolve the crystals therein completely, and the resultant solution was 10-fold diluted. Thereafter, a portion (0.5 μL) of the solution was subjected to optical purity measurement under the same conditions as described above. The results are shown in Table 4 and FIG. 4. A good linearity (Y=0.6692x+0.3945: $R^2$=0.9964) is observed between the amount of added first-form crystals and the enantiomeric excess as measured in the suspension supernatant. Meanwhile, the enantiomeric excess as measured in the solution falls within a range of measurement error. As is clear from the thus-obtained data, the amount of first-form crystals, which come to be mixed in crystals of the present invention, is detected through the evaluation method of the present invention (detection limit: 2.4% in the case where measurement error is 2%).

TABLE 4

Detection of first-form suplatast tosilate crystals contained in crystals of the present invention

| Amount of added first-form crystals (%) | Weight of added first-form crystals (mg) | Weight of added invention crystals (mg) | Optical purity measured in suspension supernatant | Optical purity measured in solution |
|---|---|---|---|---|
| 0 | 0 | 250 | 0.1% ee (S excess) | 0.0 |
| 4 | 10 | 240 | 2.5% ee (S excess) | 0.1% ee (R excess) |
| 10 | 25 | 225 | 7.9% ee (S excess) | 0.1% ee (R excess) |
| 20 | 50 | 200 | 14.6% ee (S excess) | 0.2% ee (R excess) |
| 30 | 75 | 176 | 20.0% ee (S excess) | 0.3% ee (R excess) |
| 40 | 100 | 150 | 27.0% ee (S excess) | 0.3% ee (R excess) |

(n = 1)

Example 8

Figure 5:
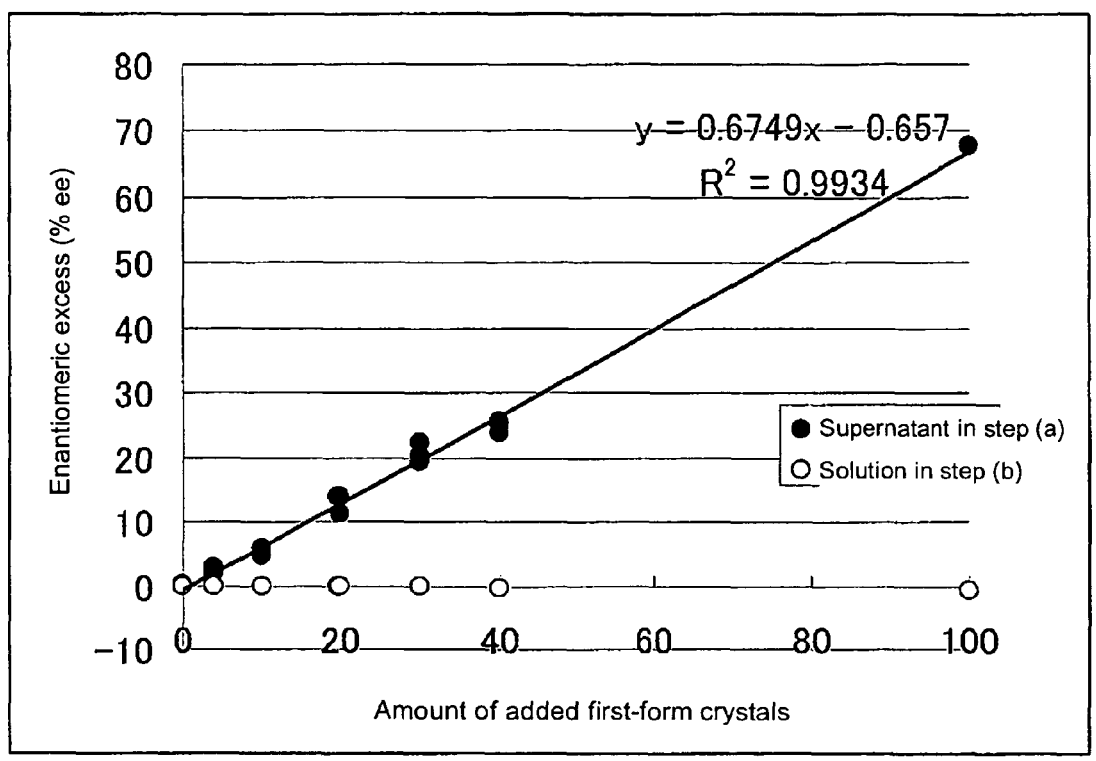
FIG. 5 Graph showing detection of first-form suplatast tosilate crystals present in third-form suplatast tosilate crystals.

Third-form suplatast tosilate crystals produced through the method described in WO 02/083633, which exhibit, as shown in FIG. 3, characteristic peaks at diffraction angles (2θ±0.1°) of 5.6°, 9.0°, 11.0°, 15.3°, 16.5°, 17.2°, 17.9°, 19.2°, 19.9°, and 21.5° as measured through powder X-ray diffractometry, and first-form suplatast tosilate crystals produced through the method described in Japanese Patent Publication (kokoku) No. 1991-70698 were placed in a sample vial in amounts shown in Table 5, and were mixed together after the vial was capped. 2-Propanol (0.5 mL) was accurately added to the resultant mixture, and the mixture was shaken for 30 seconds and then settled for 30 minutes, followed by centrifugation. A portion (1 μL) of the supernatant of the resultant suspension was applied to a chiral stationary phase column filled with cellulose tris(3,5-dimethylphenylcarbamate) (Chiralcel OD-H, 4.6 mm×25 cm, product of Daicel Chemical Industries, Ltd.) (mobile phase: mixture of n-hexane, ethanol, trifluoroacetic acid, and diethylamine (750:250:5:1)) for optical purity measurement. Subsequently, methanol (2 mL) was added to the remaining suspension to thereby dissolve the crystals therein completely, and the resultant solution was 10-fold diluted. Thereafter, a portion (0.5 μL) of the solution was subjected to optical purity measurement under the same conditions as described above. The results are shown in Table 5 and FIG. 5. A good linearity (Y=0.6749x−0.657: $R^2$=0.9934) is observed between the amount of added first-form crystals and the enantiomeric excess as measured in the suspension supernatant. Meanwhile, the enantiomeric excess as measured in the solution falls within a range of measurement error. As is clear from the thus-obtained data, the amount of first-form crystals, which come to be mixed in third-form crystals, is detected through the evaluation method of the present invention (detection limit: 3.9% in the case where measurement error is 2%).

TABLE 5

Detection of first-form suplatast tosilate crystals
contained in third-form suplatast tosilate crystals

| Amount of added first-form crystals (%) | Weight of added first-form crystals (mg) | Weight of added third-form crystals (mg) | Optical purity measured in suspension supernatant | Optical purity measured in solution |
|---|---|---|---|---|
| 0*[1] | 0 | 250 | 0.2% ee (S excess) | 0.0 |
| 4*[2] | 10 | 240 | 2.6% ee (S excess) | 0.1% ee (R excess) |
| 10*[2] | 25 | 225 | 5.1% ee (S excess) | 0.1% ee (R excess) |
| 20*[2] | 50 | 200 | 13.0% ee (S excess) | 0.2% ee (R excess) |
| 30*[2] | 75 | 175 | 20.7% ee (S excess) | 0.2% ee (R excess) |
| 40*[2] | 100 | 150 | 24.9% ee (S excess) | 0.3% ee (R excess) |
| 100*[1] | 250 | 0 | 67.7% ee (S excess) | 0.7% ee (R excess) |

*[1](n = 1),
*[2](n = 3)

Example 9

Figure 6:
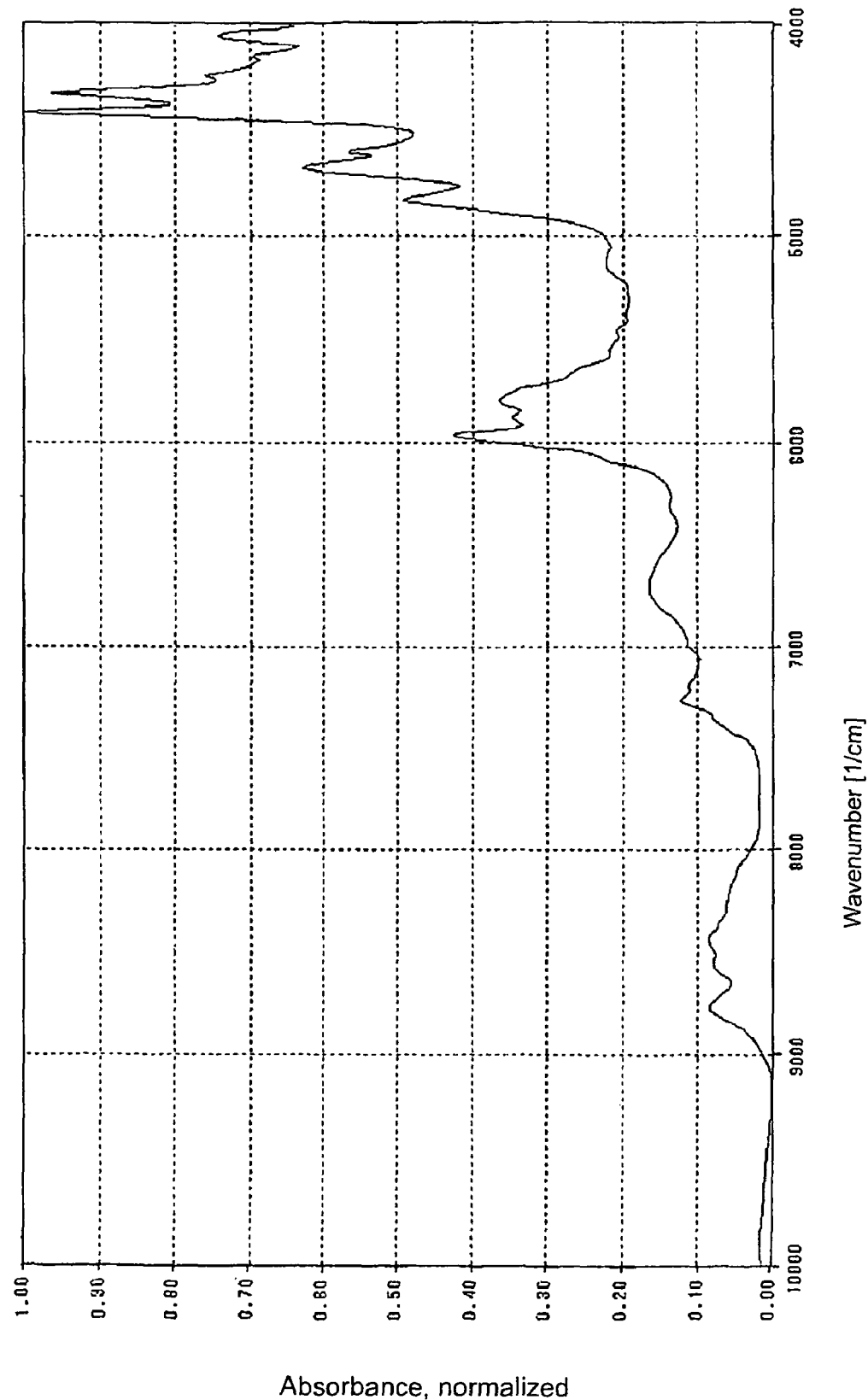
FIG. 6 Near-infrared absorption spectrum of first-form suplatast tosilate crystals.
Figure 7:
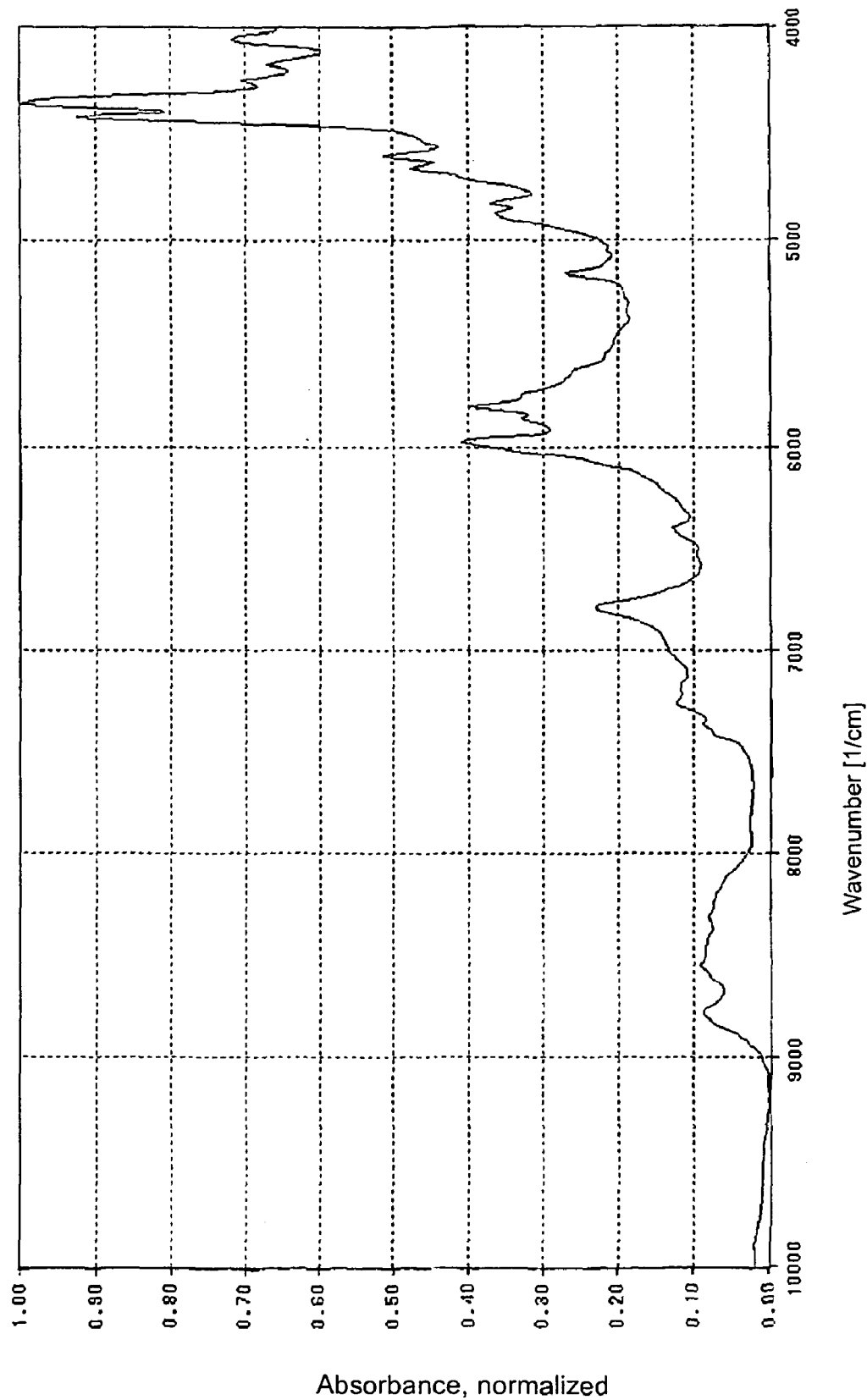
FIG. 7 Near-infrared absorption spectrum of third-form suplatast tosilate crystals.
Figure 8:
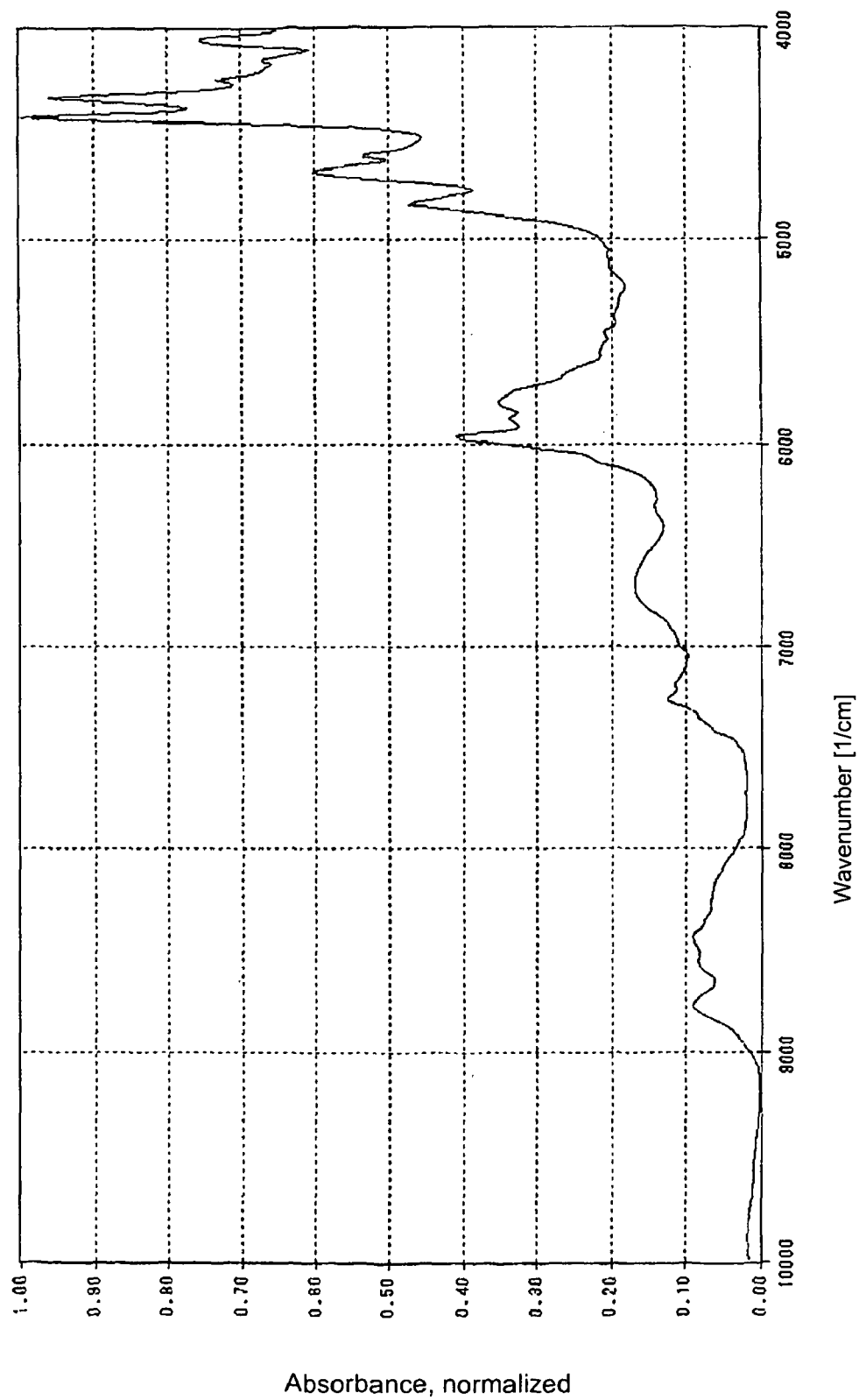
FIG. 8 Near-infrared absorption spectrum of suplatast tosilate crystals of the present invention (fourth-form suplatast tosilate crystals).

Suplatast tosilate crystals of the present invention produced in a manner similar to that described in Example 3, which exhibit peaks at diffraction angles in the vicinity of 6.7°, 13.3°, 19.0°, 20.0°, 21.7°, and 22.6°, first-form suplatast tosilate crystals, and third-form suplatast tosilate crystals were subjected to differential scanning calorimetry. The thus-measured melting points and heats of fusion are shown in Table 6. Near-infrared absorption spectra of these crystals are shown in FIGS. 6 to 8. Suplatast tosilate crystals of the present invention exhibit a melting point higher, by 5 to 6 degrees in Celsius, than that of first-form suplatast tosilate crystals. In addition, the crystals of the present invention exhibit a heat of fusion higher, by about 8 KJ/mol, than that of the first-form crystals; i.e., the crystals of the present invention are thermally stable. A difference in near-infrared absorption spectrum is observed between these crystals in a wavenumber range of 5,000 to 5,300 $cm^{-1}$.

TABLE 6

Melting points and heats of fusion of first-form suplatast
tosilate crystals, third-form suplatast tosilate crystals,
and suplatast tosilate crystals of the present invention
as measured through differential scanning calorimetry

| Sample | Melting point (° C.) | Heat of fusion (KJ/mol) |
|---|---|---|
| Invention crystals (Lot F) | 89.0 | 39.5 |
| Invention crystals (Lot G) | 89.2 | 40.1 |
| First-form crystals (Lot H) | 83.6 | 31.5 |
| First-form crystals (Lot I) | 84.2 | 31.7 |
| Third-form crystals (Lot J) | 83.0 | 39.9 |
| Third-form crystals (Lot K) | 82.8 | 39.4 |

(n = 3)

Formulation Example 1

Tablets

| | |
|---|---|
| Crystals of the present invention (Example 1) | 50 mg |
| Cornstarch | 50 mg |
| Microcrystalline cellulose | 50 mg |
| Hydroxypropyl cellulose | 15 mg |
| Lactose | 47 mg |
| Talc | 2 mg |
| Magnesium stearate | 2 mg |
| Ethyl cellulose | 30 mg |
| Unsaturated glyceride | 2 mg |
| Titanium dioxide | 2 mg |

Tablets (250 mg per tablet) having the aforementioned formulation were prepared through a customary method.

Formulation Example 2

Granules

| | |
|---|---|
| Crystals of the present invention (Example 1) | 200 mg |
| Lactose | 440 mg |
| Cornstarch | 100 mg |
| Hydroxypropyl cellulose | 50 mg |
| Talc | 10 mg |

Granules (800 mg per package) having the aforementioned formulation were prepared through a customary method.

Formulation Example 3

Capsules

| | |
|---|---|
| Crystals of the present invention (Example 1) | 100 mg |
| Lactose | 37 mg |
| Cornstarch | 50 mg |
| Microcrystalline cellulose | 10 mg |
| Magnesium stearate | 3 mg |

Capsules (200 mg per capsule) having the aforementioned formulation were prepared through a customary method.

Formulation Example 4

Dry Syrup

| | |
|---|---|
| Crystals of the present invention (Example 1) | 50 mg |
| Lactose-sucrose | 949 mg |
| Perfume | appropriate amount |

Dry syrup drugs (1,000 mg per package) having the aforementioned formulation were prepared through a customary method.

Formulation Example 5

Suppositories

| | |
|---|---|
| Crystals of the present invention (Example 1) | 300 mg |
| Witepsol W-35 (registered trademark, mixture of mono-, di-, and triglycerides of saturated fatty acids (lauric acid to stearic acid), product of Dynamite Nobel) | 1,400 mg |

Suppositories having the aforementioned formulation were prepared through a customary method.

The invention claimed is:

1. A method for evaluating evenness in the crystallinity of suplatast tosilate crystals, comprising:
   (a)(i) adding a solvent to suplatast tosilate crystals to thereby dissolve 3% or less of the crystals in the solvent and form a suspension, and (ii) subjecting a portion of the supernatant of the resultant suspension to an optical purity measurement;
   (b)(i) adding a solvent to the remaining suspension to thereby dissolve the entirety of the suplatast tosilate crystals in the suspension in the solvent, and (ii) subjecting a portion of the resultant solution to an optical purity measurement; and
   (c) comparing the optical purity measurement (a)(ii) to the optical purity measurement (b)(ii).

2. An evaluation method according to claim 1, wherein, when the optical purity as measured in each of (a)(ii) and (b)(ii) is less than 2% ee, the suplatast tosilate crystals are determined to exhibit evenness in optical purity.

3. An evaluation method according to claim 1, wherein, when the optical purity as measured in (a)(ii) is 2% ee or more, and the optical purity as measured in (b)(ii) is less than 2% ee, the suplatast tosilate crystals are determined to contain uneven crystals.

4. An evaluation method according to claim 2 or 3, wherein the solvent employed in (a)(i) is a single member selected from the group consisting of 1-propanol, 2-propanol, 2-methylpropanol, 2-butanol, acetone, ethyl acetate, dioxane, diethyl ether, acetonitrile, tetrahydrofuran, and mixtures thereof; and the solvent employed in (b)(i) is a single member selected from the group consisting of water, methanol, ethanol, dichloromethane, chloroform, and acetonitrile, and mixtures thereof.

5. The method for evaluating evenness in the crystallinity of suplatast tosilate crystals according to claim 1, wherein the suspension formed in (a)(i) is allowed to settle until the supernatant forms.

6. The method for evaluating evenness in the crystallinity of suplatast tosilate crystals according to claim 5, wherein the suspension in (a)(i) is shaken and allowed to settle until the supernatant forms.

7. A method for evaluating evenness in the crystallinity of suplatast tosilate crystals according to claim 1, wherein the optical purity is measured by absorption spectroscopy.

8. A method for evaluating evenness in the crystallinity of suplatast tosilate crystals according to claim 1, wherein the optical purity is measured by a chiral column.

9. A method for evaluating evenness in the crystallinity of suplatast tosilate crystals according to claim 1, wherein the optical purity is measured by powder X-ray diffractometry.

10. A method for evaluating evenness in the crystallinity of suplatast tosilate crystals according to claim 1, wherein the optical purity is measured by differential scanning calorimetry.

* * * * *